United States Patent [19]

Stabinsky

[11] Patent Number: 4,797,355
[45] Date of Patent: Jan. 10, 1989

[54] METHODS FOR ATTACHING POLYNUCLEOTIDES TO SUPPORTS

[75] Inventor: Yitzhak Stabinsky, Boulder, Colo.
[73] Assignee: Amgen Inc., Thousand Oaks, Calif.
[21] Appl. No.: 744,507
[22] Filed: Jun. 13, 1985
[51] Int. Cl.$^4$ .................. C12Q 1/68; G01N 33/566
[52] U.S. Cl. ........................................... 435/6; 436/501; 935/77; 935/78
[58] Field of Search ............ 435/6, 7; 436/501; 536/28, 29; 935/77, 78

[56] References Cited

U.S. PATENT DOCUMENTS 4,358,535 7/1982 Falkow et al. ................... 435/5
4,415,732 3/1983 Caruthers et al. ................ 536/27

FOREIGN PATENT DOCUMENTS 062286 5/1982 European Pat. Off. .

OTHER PUBLICATIONS

Cozzarelli, et al., *Biochem. Biophys. Res. Comm.* 28, 578–586 (1967).
Dunn, et al., Cell, 12, 23–36 (1977).
Maniatis, et al., *Molecular Coning:* A Laboratory Manual, Cold Spring Harbor Laboratory, New York (1982) (Standard Text Not Enclosed).
Ranki, et al., *Gene,* 21, 77–85 (1983).
Thomas, *Proc. Natl. Acad. Sci. (U.S..A),* 77, 5201–5205 (1980).
Wu et al., *Proc. Natl. Acad. Sci. (U.S.A.),* 78 7059–7063 (1981).

*Primary Examiner*—Robert J. Warden
*Assistant Examiner*—Jack Spiegel
*Attorney, Agent, or Firm*—Marshall, O'Toole, Gerstein, Murray, Bicknell

[57] ABSTRACT

A probe is attached to a stock support to which is bound a single-stranded polynucleotide by hybridizing both the probe and the bound polynucleotide to a connecting strand with which they are both complementary and then ligating an end of the bound polynucleotide and the probe. After denaturation, the probe remains attached to the support by way of the bound polynucleotide. A target polynucleotide is then hybridized with the support-bound probe and with a labelled probe to provide a detectable hybridization complex.

3 Claims, 1 Drawing Sheet

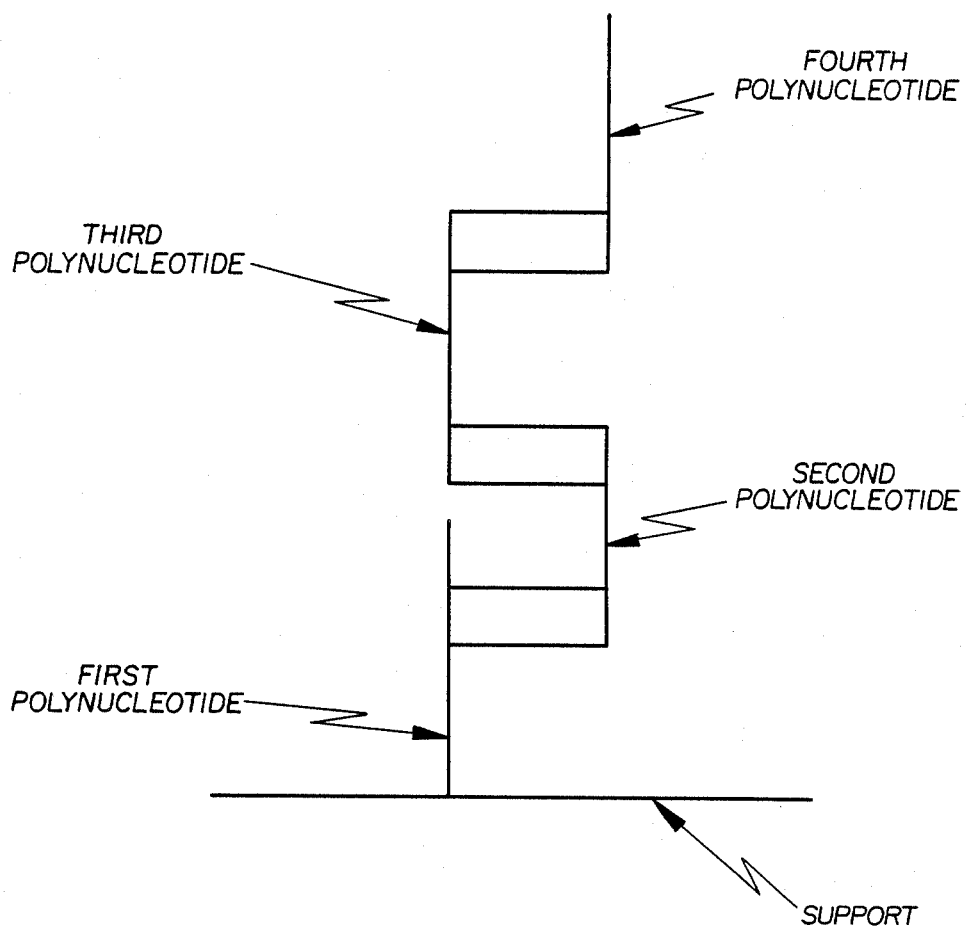

METHODS FOR ATTACHING POLYNUCLEOTIDES TO SUPPORTS

BACKGROUND

The present invention relates in general to methods for attaching polynucleotides to supports and in particular to methods for attaching a nucleic acid hybridization probe to a solid support.

One characteristic property of nucleic acid, which forms the heritable material of all living organisms, is its ability to form sequence-specific hydrogen bonds (i.e., to hybridize) with a nucleic acid having a complementary nucleotide sequence. This ability of nucleic acids to hybridize with complementary strands of nucleic acid has been exploited in techniques generally called hybridization assays.

In a hybridization assay, a nucleic acid having a known sequence is used as a probe to search a sample for a "target" complementary sequence. Labelling of the hybrid formed by the probe and the target permits the detection and quantitation of complementary sequence.

Because all strains of a particular micro-organism share a genetic component in the form of nucleic acids susceptible to diagnosis by means of a hybridization assay, hybridization assays are valuable research and medical tools. Detection of specific target nucleic acids enables accurate diagnosis of bacterial, fungal and viral disease states in humans, animals and plants. Additionally, the ability to probe for a specific nucleotide sequence is of potential use in the identification and diagnosis of human genetic disorders.

In one type of hybridization assay, called solution hybridization, a labelled polynucleotide probe is added to a solution of a sample to be searched for a target nucleic acid. In order to ensure that both the probe and a target are in a single-stranded state suitable for hybridization, the sample and probe are heated in order to break (denature) the hydrogen bonds which are found between complementary strands of a double-stranded probe or target, or which are found within the secondary structure of a single-stranded probe or target. Upon cooling, the reaction is reversed and double-stranded nucleic acid is allowed to form. The amount of double-stranded nucleic acid which forms may be determined by scintillation counting of the label on the probe after degradation of unhybridized single strands or after isolating double-stranded DNA by passing the hybridization solution over a hydroxyapatite column which selectively retains the double-stranded form. However, if either the probe or the target was introduced in double-stranded form, a reaction reforming (renaturing) double-stranded probe or a double-stranded target competes with the hybridization reaction between probe and target and thereby reduces the sensitivity of this technique.

In another approach to hybridization assays, renaturation is prevented by immobilizing denatured target nucleic acid on a support. After passage of the support-bound target through a solution containing labelled probe, retention of the probe on the support-bound target permits detection and quantitation of the target by measurement of the amount of bound label. See, e.g., Falkow, et al., U.S. Pat. No. 4,358,535; and Shafritz, European Patent Application No. A1-0062286. However, because the amount of labelled probe is far in excess of the amount of target present, non-specific binding of the labelled probe to the support may swamp the detectable signal from a small amount of target.

Still another approach to hybridization assays is called a "sandwich" hybridization. A two-step sandwich hybridization procedure involves the use of an immobilized target nucleic acid which is exposed in a first step to a first nucleic acid probe having a first portion complementary to the target and having a second portion which is not complementary to the target. In a second step, a second, labelled nucleic acid probe which is complementary to the second portion of the first probe is allowed to hybridize to the first probe, forming a "sandwich" with the first probe between the target and the second probe. Dunn, et al., Cell, 12: 23–36 (1977). The sandwich hybridization procedure is relatively easy to perform and is not seriously affected by protein or other biological contaminants. Ranki, et al., Gene, 21 77–85 (1983). However, a two-step sandwich hybridization assay involves considerable delay associated with immobilization of the sample on a filter.

It is neither easy nor convenient to attach a single-stranded nucleic acid probe directly to a solid support for use in a sandwich hybridization assay. For example, the attachment of a nucleic acid to a nitrocellulose sheet involves fixing the nucleic acid by contact with the sheet for 12–15 hours and baking the nucleic acid onto the sheet for two hours. See, e.g., Thomas, Proc. Natl. Acad. Sci. (USA), 77: 5201 (1980). Such preparation of a DNA-coated nitrocellulose sheet may easily consume as much as a full working day, a factor which limits the clinical usefulness of nucleic acid hybridization.

Furthermore, because the nucleic acid probe is sequence-specific for a particular target molecule, the procedure for attaching the probe to the support must be performed for each target molecule to be detected. Thus, in order to detect a number of different DNA sequences, a diagnostic laboratory must prepare an equal number of types of supports.

SUMMARY OF THE INVENTION

Accordingly, a method according to the present invention involves preparing a support in a hybridization assay. In this method, a first single-stranded polynucleotide is attached to a support so that the first single-stranded polynucleotide has a free first end. A first portion of a second single-stranded polynucleotide is hybridized with the first single-stranded polynucleotide so that the second single-stranded polynucleotide has a free single-stranded end. A third single-stranded polynucleotide is connected by hybridization to a second portion of the second single-stranded polynucleotide. The first and second portions of the mediator and target polynucleotides are preferably separate and distinct (i.e., non-overlapping) in order to prevent interference. The second and third single-stranded polynucleotides are connected so that a first end of the third single-stranded polynucleotide is adjacent the first end of the first single-stranded polynucleotide. The first end of the first single-stranded polynucleotide is ligated to the first end of the third single-stranded polynucleotide to form a probe polynucleotide bound to the support. The second single-stranded polynucleotide is denatured from the probe polynucleotide and a fourth polynucleotide is immobilized by hybridization to the probe polynucleotide.

Other aspects and advantages of the present invention will become obvious to one skilled in the art upon consideration of the present invention.

BRIEF DESCRIPTION OF THE DRAWING

FIG. 1 is a schematic illustrating the hybridization assay according to the present invention.

DETAILED DESCRIPTION

In order to provide a convenient method for attaching a probing sequence to a solid support in a way that is useful for hybridization assays, the present invention provides a support with an attached polynucleotide. A nucleic acid probe for capturing a target is ligated to the attached polynucleotide using standard solution procedures. The probe may be in single- or partially double-stranded form, but if it is in single-stranded form, a connecting polynucleotide must be hybridized to both the support-attached polynucleotide and to the probe in order to place the probe adjacent to the support-attached polynucleotide in position (5' end next to 3' end) for ligation.

A polynucleotide strand may be linked to a support-bound polynucleotide according to the procedure of the ligase assay disclosed in Cozzarelli, et al., *Biochem. Biophys. Res. Comm.*, 28: 578–586 (1967). In this ligase assay, a substrate, consisting of an oligomer of five to ten deoxythymidylate residues (dT) is prepared by esterification through its 5'-phosphoryl terminus to one of the glucose hydroxyl groups of cellulose. The dT oligomer is, in turn, joined by a phosphodiester linkage to a polymer of 100 to 200 deoxycytidylate residues with a free 3' hydroxyl group at its terminus. This sequence of cytidine residues is hydrogen-bonded to a strand of approximately 1,800 deoxyinosinate residues, which is in turn hydrogen bonded to a strand of approximately 1,800 $^3$H-labelled deoxycytidylate residues with free 5'-phosphoryl and 3'-hydroxyl termini. A sample to be tested for ligase is applied, followed by alkaline denaturation. If ligase is present in the sample, the $^3$H-labelled deoxycytidylate strand has been joined by the action of the ligase to the support and remains bound to the support. If the sample contains no ligase, only unlabelled support remains after washing because no $^3$H-labelled deoxycytidylate has been ligated to the support-bound deoxycytidylate.

Accordingly, in the method according to the present invention, a deoxythymidylate polymer having a free 5'-hydroxyl end is synthesized on a solid support. Application of T$_4$ DNA kinase and ATP to this system results in the phosphorylation of the 5' terminus of the deoxythymidylate polymer. To this first, support-bound polynucleotide, a second polynucleotide, having a polyadenosine tail at a single-stranded end, is hybridized with the support-bound polynucleotide. A third polynucleotide, previously hybridized with the second polynucleotide or hybridized with it at this point, is ligated by means of T$_4$ DNA ligase to the support-bound polynucleotide. After either heat or alkaline denaturation and washing, the third polynucleotide remains as a hybridization probe bound to the support by way of the polythymidine polymer.

A fourth polynucleotide, which may be a target, is immobilized by hybridization to the immobilized probe. A labelled polynucleotide probe is hybridized with the fourth polynucleotide to form a "sandwich".

Conventional methods may be used to detect or quantify the target by measuring the amount of label on the immobilized sandwich hybrid and may also involve separating the immobilized hybrid from the solution. A detectable label may be radioactive, such as $^{125}$I, $^{35}$P, and the like, or non-radioactive (e.g., fluorescent or immunological).

The method of the present invention may be employed where the target polynucleotide is a deoxyribonucleic or ribonucleic acid. In either case, depending on preference for a DNA-DNA, RNA-RNA, or DNA-RNA hybridization between a support-bound probe and a labelled probe target, the support-bound and labelled probe sequences may be deoxyribonucleic or ribonucleic acid sequences.

Any solid support to which a sequence may be bound is useful in this method, including both porous and non-porous supports, e.g., such as silica gel, controlled pore glass, and nitrocellulose paper. Most commercially available supports contain or may be provided with amine or carboxylic acid functional groups to which DNA may be linked. Alternatively, a bead coating providing multiple points of attachment for a polynucleotide may be employed.

One immobilized polynucleotide for use according to the present invention is a poly-thymidine strand which may be synthesized on a support without the need for deprotection at the end of the synthesis. The complementary polynucleotide may be poly-adenosine. Where poly T/poly A hybridization is employed, the hybridization assay for the target polynucleotide is preferrably conducted at a temperature lower than the melting point of AT pairs to prevent the mediator probe from disengaging from the mediator.

In the following examples, the method according to the present invention is described in detail. In Example 1, the attachment of polythymidine (poly T) to a support is described. Example 2 demonstrates ligation of the probe polynucleotide to a support-bound polynucleotide and a hybridization assay employing the ligated probe. Example 3 describes a method of attaching a restriction fragment as a probe according to the present invention.

EXAMPLE 1

Polythymidine (poly T) was synthesized on amine-functionalized controlled pore glass (CPG) (available from Pierce Chemical Company, Rockford, Ill.) and on Fractosyl-500 (F-500) glass beads (available from Polysciences, Inc., Warrington, Pa.).

An amine function was attached to F-500 by treating 500 mg of F-500 with a solution of 700 $\mu$l of H$_2$N(CH$_2$)$_3$Si(OCH$_2$CH$_3$)$_3$ in 10 ml of 95% ethanol at room temperature for 3 hours. The treated F-500 was washed once with methanol and then once with ethyl ether. The F-500 was dried at room temperature and then baked at 110° C. for 15 hours. It was then washed with water, methanol and water, and then dried. The product was (F-500)O(CH$_2$)$_3$NH$_2$, an amine-functionalized F-500.

Next, the amine-functionalized CPG and the amine-functionalized F-500 were prepared for poly T synthesis.

500 mg of the amine-functionalized CPG was reacted for 30 minutes at room temperature with 250 mg (1 millimole) of phthallic anhydride in the presence of 2 ml of anhydrous pyridine and 61 mg of 4-dimethyl amino pyridine to produce the product:

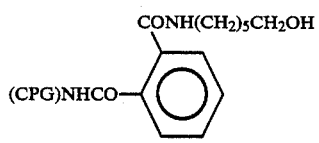

(1)

The product was rinsed with methylene dichloride, ethyl alcohol and ether, and then dried. 450 mg of the product was reacted with 330 mg of dicyclohexylcarbodiimide (DCC) for 30 minutes at room temperature. The solution was decanted and replaced with a solution of 117 mg of 6-amino-1-hexanol in 2 ml of methylene dichloride and then left at room temperature for approximately 8 hours.

The amine-functionalized F-500 was prepared for poly T synthesis by treatment with 400 mg of succinic anhydride and 244 mg of 4-dimethyl aminopyride in 3 ml of anhydrous pyridine for 18 hours at room temperature. The treated F-500 was then washed with N,N-dimethylformamide (DMF), methanol and ethyl ether. A ninhydrin test showed that 98% of the free amino groups had reacted to produce approximately 400 mg of (F-500)O(CH$_2$)$_3$NHCO(CH$_2$)$_2$COOH. This product was suspended in 2 ml of DMF containing 3 millimoles (330 mg) of DCC and 3 millimoles (420 mg) of p-nitrophenol at room temperature overnight. The product,

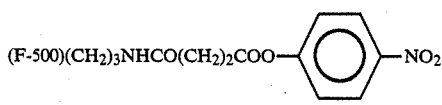

(2)

was washed on a sintered glass funnel with DMF, CH$_3$CN, CH$_2$Cl$_2$ and ethyl ether. A solution of 2 millimoles (234 mg) of H$_2$N(CH$_2$)$_6$OH in 2 ml of DMF was reacted with product (2) overnight. The product of this reaction was a support, (F-500)-O(CH$_2$)$_3$NHCO(CH$_2$)$_2$CONH(CH$_2$)$_5$C-H$_2$OH        (3)

which was washed with DMF, CH$_3$CN, methanol and ethyl ether.

The functionalized ester resulting from the preparation of CPG as outlined above, and product (3) were used as supports for the synthesis of a poly T chain. Each thymidine (T) residue was added as a phosphoramidite according to the procedure of Caruthers, et al., U.S. Pat. No. 4,415,732, in a cycle of phosphoramidite synthesis as described therein.

51 cycles of phosphoramidite synthesis were performed to provide (CPG) p(Tp)$_{50}$T-OH 5' and (F-500) p(Tp)$_{50}$T-OH 5'. A 25 mg unit of each of these two poly T supports was phosphorylated in 100 μl of 1×ligation buffer [0.05 M Tris, pH 7.4; 0.01 M MgCl$_2$; 0.01 M dithiothreitol (DTT); 1 mM spermidine; 1 mg/ml bovine serum albumin (BSA)] containing 50 nanomoles of $^{32}$P-γ-ATP (specific activity, 300 cpm/picomole) and 6 units of T-4-polynucleotide kinase for 2 hours at 37° C. The supports were then washed with water, 5×SSPE (0.9 M NaCl; 0.06 M NaH$_2$PO$_4$, pH 7.5; and 5 mM EDTA) at 90° C. The supports were then washed with 90° C. water and dried. The loading of the CPG beads was determined to be 760 picomoles of poly T per milligram and the loading of the F-500 support was determined to be 260 picomoles of poly T per milligram.

EXAMPLE 2

Four synthetic polynucleotides were synthesized using the techniques of Caruthers, et al., supra, and were hybridized and ligated in 1×ligation buffer containing 7 mM ATP and 4.5 units of T-4 ligase to form (A) 5'-$^{32}$P—CTT CAG CGC GAA CGA CCA ACT ACC CCG        (4)
            C GCG CTT GCT GGT TGA TGG GGC ATC ATC AGT TAT CCT TAA GGT CTC
TAG TAG TCA ATA GGA ATT CCA GAG AAAAA-5'        (B)

The poly A 5' end of the (B) strand of double-stranded polynucleotide (4) (approximately 400 picomoles) was incubated at room temperature overnight in 100 μl of ligation buffer (as above) containing 1 M DTT, 10 mM ATP and 3 units of T-4 DNA ligase and CPG-p(Tp)$_{16}$ supports prepared as in Example 1. The products were then washed with 100 μl of ligation buffer and with water at 90° C. until no more counts could be washed. Thus, the (A) strand of polynucleotide (4) was ligated to the support, while the (B) strand of polynucleotide (4) was removed by denaturation in the course of the washings at 90° C. to leave a complex having the (A) strand of polynucleotide (4) as an immobilized probe.

Two synthetic polynucleotides, one of which was labelled with $^{32}$P-γ-ATP as above, were synthesized using the technique of Caruthers, et al., supra, and were hybridized to form (C) 5'-$^{32}$P—CCG ATC ATC AGT TAT CCT TAA GGT        (5)
            G TAG TCA ATA GGA ATT CCA

CTC
GAG AAAAA-5' (D)

Double-stranded polynucleotide (5) (approximately 400 picomoles) was incubated at room temperature overnight in 50 μl of ligation buffer (as above) containing 10 millimolar ATP, 1 M DTT and 3 units of T$_4$ DNA ligase and CPG-p(Tp)$_{16}$ supports prepared as in Example 1. The products were then washed with 100 μl of ligation buffer and with water at 90° C. until no more counts could be washed. Thus, the (C) strand of polynucleotide (5) was ligated to the support while the (D) strand of polynucleotide (5) was removed by denaturation in the course of the washings at 90° C. to leave a complex having the (C) strand of polynucleotide (5) as an immobilized probe.

The immobilized probe (C), as described above, was measured by scintillation counting at 112,000 cpm/10 mg of support, indicating a loading of 11.2 picomoles per milligram. Likewise, the immobilized probe (A), as described above, was measured by scintillation counting at 45,800 cpm/10 mg of support, indicating a loading of 4.6 picomoles per milligram.

In the following hybridization experiments, a segment (E) has the sequence (E) 3'-GTA GTC AAT GGA ATT CCA CAG
         AAAAA-5'        (6)

and a target polynucleotide (F) has a sequence (F)
3'-CGC GCT TGC TGG TTG ATG GGG CT-5'        (7)

Thus, target polynucleotide (E) is complementary to probe (C) and to part of probe (A). On the other hand, polynucleotide (F) has no complementary sequence on polynucleotide (C) but has such a complementary sequence on polynucleotide (A). In a series of experiments, as set forth in Table III, the indicated probe polynucleotides were incubated at 45° C. for 60 minutes with the indicated immobilized polynucleotide in ligation buffer as described above.

TABLE III

| Experiment Number | Unlabelled Immobilized Polynucleotide on CPG (amount) | Probe Polynucleotide |
|---|---|---|
| 1 | C (1.3 mg) | E |
| 2 | A (1.3 mg) | E |
| 3 | C (1.9 mg) | E |
| 4 | C (1.5 mg) | F |
| 5 | A (1.5 mg) | F |
| 6 | A (1.8 mg) | E and F |

After hybridization, the beads were washed five times with 6×SSC buffer until no counts were observed in the washings. The results appear in Table IV.

TABLE IV

| Experiment of Number | cpm on the Bead Before Hybridization | cpm on the Bead After Hybridization and Washings | Efficiency Hybridization |
|---|---|---|---|
| 1 | 16,000 | 210,000 | 90% |
| 2 | 5,600 | 73,000 | 93% |
| 3 | 24,000 | 326,000 | 97% |
| 4 | 18,000 | 18,700 | (no hybridization should occur) |
| 5 | 6,700 | 104,000 | 100% |
| 6 | 8,000 | 200,000 | 95% |

The results indicated in Table IV demonstrate that the efficiency of hybridization according to the present invention may be as high as 90% to 100%.

EXAMPLE 3

Following the procedures described above, a CPG-p(Tp)$_{16}$ support may be prepared. A restriction fragment of cloned DNA may be obtained and a poly A tail added to the 3' end of each strand by means of the terminal transferase procedure of Wu, et al., *Proc. Natl. Acad. Sci.* (U.S.A.), 78: 7059–7063 (1981).

This double-stranded polynucleotide may be cut with any of a number of restriction endonucleases, for example, those listed in Maniatis, et al., *Molecular Cloning: A Laboratory Manual*, Cold Spring Harbor Laboratory, N.Y. (1982), either before or after hybridization of the poly A tail with the poly T bound to the support. Also, a double-stranded polynucleotide may be manufactured to have an overhanging end with the desired sequence, as shown in Example 2.

A double-stranded DNA to be attached as a probe may then be cut with the same restriction endonuclease used to cut the first double-stranded polynucleotide or provided with an appropriate complementary overhang. Hybridization of the single-stranded portions of the double-stranded polynucleotides, ligation of the strands with T$_4$ DNA ligase, and a denaturing wash result in a strand of the second double-stranded polynucleotide being connected by way of a strand of the first double-stranded polynucleotide and the poly T strand to the support.

It is expected that numerous modifications and variations will occur to those skilled in the art upon consideration of the present invention. For example, other sorts of linkage system may also be employed. For example, poly T may be directly synthesized on F-500. In a demonstration of this system, 500 mg of glass beads (available from Polysciences, Inc., Warrington, Pa., as Catalog No. 5483) were incubated with 2 ml of 0.5 molar tetrazole and 0.5 molar T-phosphoramidites for 2 hours in anhydrous CH$_3$CN, and then washed with CH$_3$CN and treated with an iodine solution for 5 minutes. Thereafter, phosphoramidite synthesis according to Caruthers, et al., supra, was used to obtain F-500-T$_{25}$.

Consequently, it is intended that the present invention be given the full scope of the appended claims.

What is claimed is:

1. A method for a hybridization assay comprising the steps of:
   attaching a first single-stranded polynucleotide to a support so that the first single-stranded polynucleotide has a first free end;
   hybridizing a first portion of a second single-stranded polynucleotide with the first single-stranded polynucleotide so that the second single-stranded polynucleotide has a free single-stranded end;
   connecting by hybridization a third single-stranded polynucleotide to a second portion of the second single-stranded polynucleotide, separate and distinct from the first portion of the second single-stranded polynucleotide, so that the third single-stranded polynucleotide has a first end adjacent the first end of the first single-stranded polynucleotide;
   ligating the first end of the first single-stranded polynucleotide to the first end of the third single-stranded polynucleotide to form a probe polynucleotide bound to the support;
   denaturing the second single-stranded polynucleotide from the probe polynucleotide; and
   immobilizing a fourth polynucleotide constituting a target analyte by hybridization to the probe polynucleotide.

2. The method as recited in claim 1 further comprising the steps of:
   prior to the step of denaturing the second single-stranded polynucleotide from the probe polynucleotide,
   providing the second single-stranded polynucleotide with a free single-stranded end having a first nucleotide sequence;
   hydrogen bonding at least a portion of the first nucleotide sequence to a complementary sequence on a single-stranded end of a fifth polynucleotide; and
   joining the fifth polynucleotide to the third single-stranded polynucleotide by ligation to form a probe polynucleotide bound to the support.

3. The method as recited in claim 2 wherein the fifth polynucleotide is a double-stranded polynucleotide and further comprising the step of removing one strand of the fifth polynucleotide by denaturation.

* * * * *